US00PP25923P2

(12) United States Plant Patent
Zampini

(10) Patent No.: US PP25,923 P2
(45) Date of Patent: Sep. 22, 2015

(54) *BERBERIS* PLANT NAMED '24KAGOZAM'

(50) Latin Name: *Berberis thunbergii*
Varietal Denomination: 24kagozam

(71) Applicant: James W. Zampini, Fairport Harbor, OH (US)

(72) Inventor: James W. Zampini, Fairport Harbor, OH (US)

(73) Assignee: LAKE COUNTRY NURSERY, Perry, OH (US)

( * ) Notice: Subject to any disclaimer, the term of this patent is extended or adjusted under 35 U.S.C. 154(b) by 183 days.

(21) Appl. No.: 13/815,635

(22) Filed: Mar. 13, 2013

(51) Int. Cl.
*A01H 5/12* (2006.01)

(52) U.S. Cl.
USPC ..... Plt./241

(58) Field of Classification Search
USPC ..... Plt./241
See application file for complete search history.

(56) References Cited

PUBLICATIONS

Federal Register, vol. 75, issue 173, pp. 54461-54462, Sep. 8, 2010.*
Squak Mt. Greenhouses & Nursery, http://plants.squakmtnursery.com/12230001/Plant/10900/24_Karat_Gold_Dwarf_Barberry, downloaded Apr. 3, 2015.*
Lake County Nursery, www.lakecountynursery.com/lcns%20sell%20sheets/24KaratGold.pdf, downloaded Apr. 3, 2015.*
Van Essen Nursery Company, http://www.nanessennursery.com/index.cfm?fuseaction=plants.plantDetail&plant_id=552, downloaded Apr. 3, 2015.*

* cited by examiner

*Primary Examiner* — Anne Grunberg
(74) *Attorney, Agent, or Firm* — Penny J. Aguirre

(57) ABSTRACT

A new cultivar of *Berberis*, '24kagozam', characterized by its low growing, compact, and rounded plant habit, its very slow growth habit, and its foliage that is gold in color with the stems and foliage of the new growth orange in color.

3 Drawing Sheets

Botanical classification: *Berberis thunbergii.*
Variety denomination: '24kagozam'.

BACKGROUND OF THE INVENTION

The present invention relates to a new and distinct cultivar of *Berberis thunbergii*, and will be referred to hereafter by its cultivar name, '24kagozam'. '24kagozam' is a new cultivar of shrub grown for use as an ornamental landscape plant.

The Inventor discovered the new cultivar as a chance seedling in a seedbed at his nursery in Perry, Ohio in 2004. The seedbed had been planted with seeds from an unnamed plant of *Berberis thunbergii.*

Asexual propagation of the new cultivar was first accomplished by the Inventor using softwood stem cuttings in summer of 2009 in Perry, Ohio. Asexual propagation of the new cultivar by softwood stem cuttings has been determined that the characteristics are stable and are reproduced true to type in successive generations.

SUMMARY OF THE INVENTION

The following traits have been repeatedly observed and represent the characteristics of the new cultivar as grown outdoors in a trial plot in Perry, Ohio. These attributes in combination distinguish '24kagozam' as unique cultivar of *Berberis.*

1. '24kagozam' exhibits a low growing, compact, and rounded plant habit.
2. '24kagozam' exhibits a very slow growth habit.
3. '24kagozam' exhibits foliage that is gold in color with the stems and foliage of the new growth orange in color.

The parent plant of '24kagozam', an unnamed plant of *Berberis thunbergii*, differs from '24kagozam' in having red foliage, a more vigorous growth habit, and a plant habit that is larger is size, less compact, and is less branched. '24kagozam' can be most closely compared to the cultivars 'Bogozam' (not patented) and 'Monlers' (U.S. Plant Pat. No. 9,577). Both cultivars differ from '24kagozam' in being larger in size, in having less dense branching, having more vigorous plant habits, and in lacking new growth that is orange in color. In addition, 'Monlers' is less cold hardy than '24kagozam'.

BRIEF DESCRIPTION OF THE DRAWINGS

The accompanying colored photographs were taken in mid summer and illustrate the overall appearance and distinct characteristics of a nine year-old plant of the new *Berberis* as grown outdoors in a trial bed in Perry, Ohio.

The photograph in FIG. 1 provides an overall view of the plant habit and foliage coloration of '24kagozam' in spring.

Figure 1:
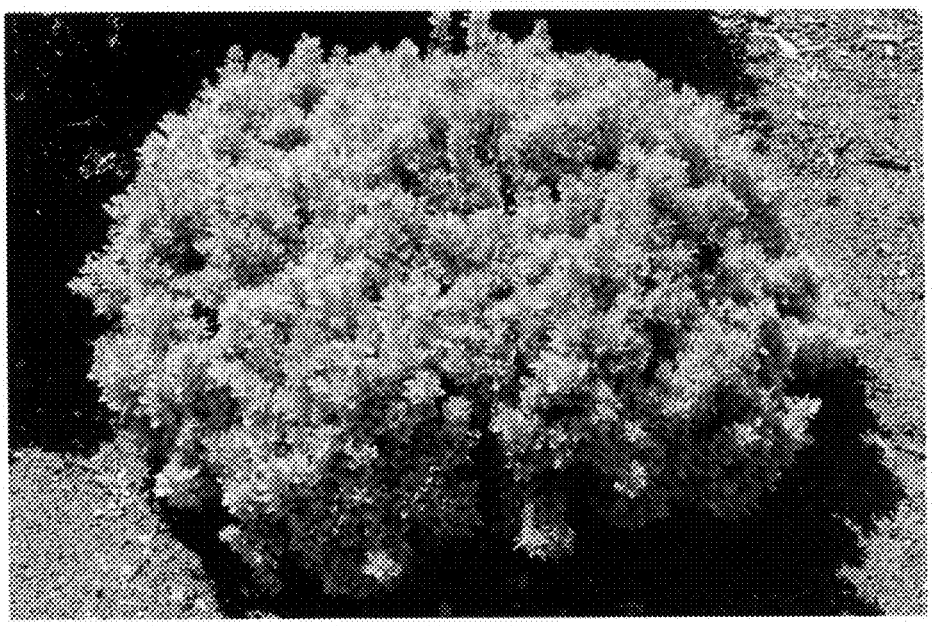
Figure 2:
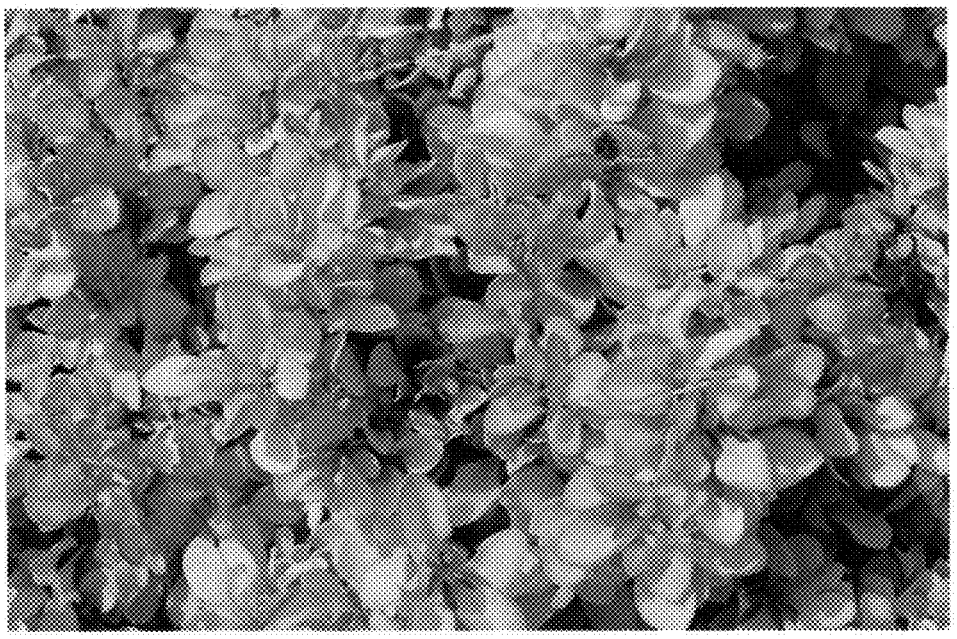

The photograph in FIG. 2 provides a close-up view of the foliage of '24kagozam' in spring.

Figure 3:
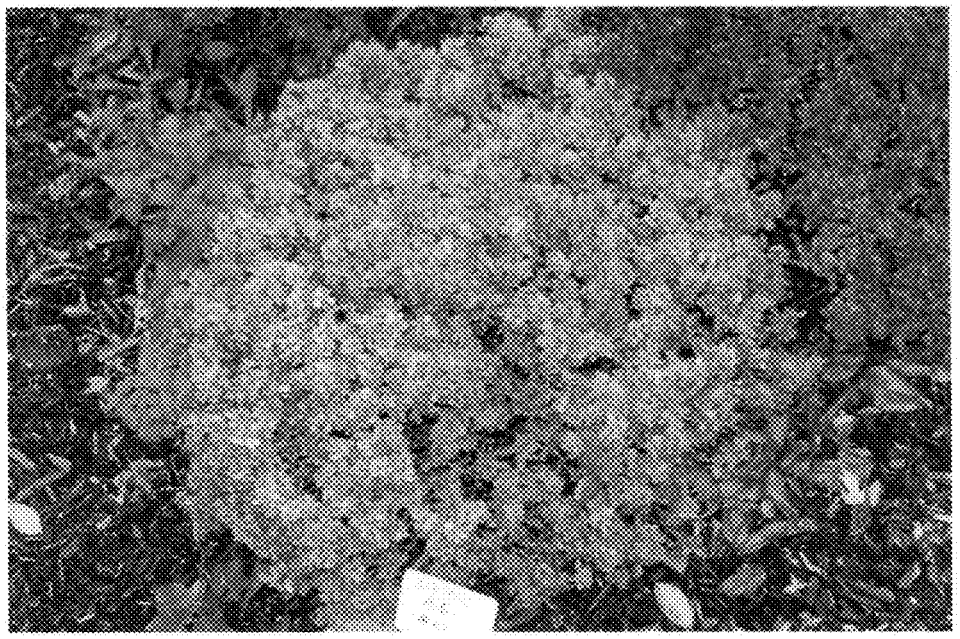

The photograph in FIG. 3 provides a view of the foliage coloration of '24kagozam' in fall.

Figure 4:
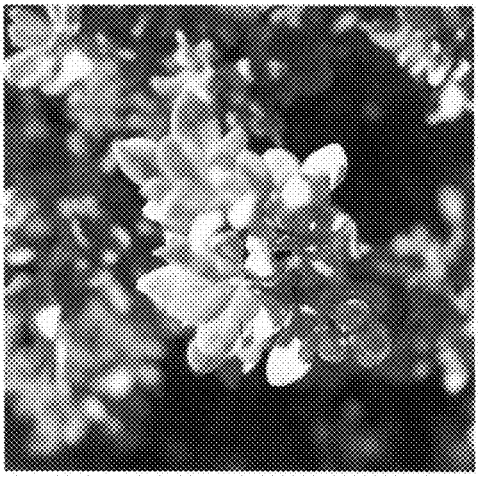

The photograph in FIG. 4 provides a close-up view of the flower buds of '24kagozam'.

Figure 5:
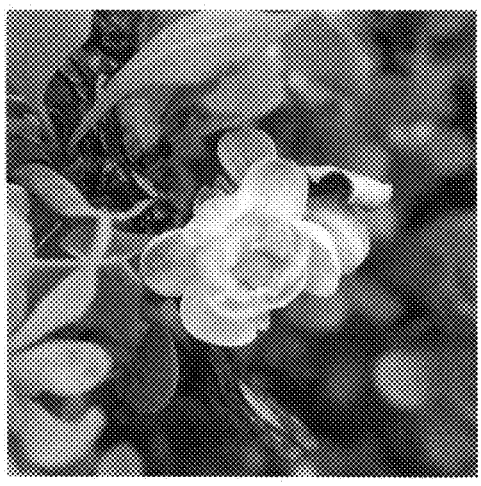

The photograph in FIG. 5 provides a close-up view of a flower of '24kagozam'.

Figure 6:
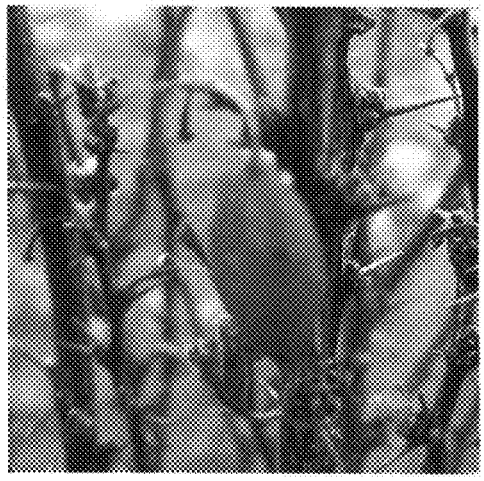

The photograph in FIG. 6 provides a close-up view of the fruit of '24kagozam'.

The colors in the photographs may differ slightly from the color values cited in the detailed botanical description, which accurately describe the colors of the new *Berberis*.

DETAILED BOTANICAL DESCRIPTION

The following is a detailed description of 3 year-old plants the new *Berberis* as grown in 3-gallon containers in Perry, Ohio. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—April to May in Ohio.

*Plant type*.—Deciduous shrub.

*Plant habit*.—Low growing, compact, and rounded.

*Plant height and spread*.—Reaches 46 cm (18 inches) in height and 91 cm (36 inches) in spread.

*Diseases and pests*.—The new cultivar has been observed to be disease free to date under the conditions of trials.

*Sun tolerance*.—High, no foliage burning has been observed when grown in full sun with sufficient moisture.

*Cold hardiness*.—At least in U.S.D.A. Zone 4.

*Root description*.—Fibrous.

*Propagation*.—Softwood stem cuttings.

*Growth rate*.—Very slow.

Stem description:

*Shape*.—Round.

*Stem color*.—New growth; 151A and suffused with 33A, maturing;160A, mature bark a blend of 200B and 200D.

*Stem size*.—Main branches; about 10 cm in length and 3 mm in diameter, lateral branches; average of 7 cm in length and 1.5 mm in diameter.

*Stem surface*.—New growth; glabrous and slightly glossy, mature wood is dull and smooth and becoming bark-like as it ages.

*Internode length*.—An average of 4 mm.

*Branching*.—An average of 5 lateral branches per main stem, alternate pattern, narrow angles.

Foliage description:

*Leaf shape*.—Spatulate.

*Leaf division*.—Simple.

*Leaf base*.—Long attenuate.

*Leaf apex*.—Rounded to broadly acute with small apiculate tip.

*Leaf venation*.—Pinnate.

*Leaf margins*.—Entire.

*Leaf attachment*.—Sessile.

*Leaf arrangement*.—Alternate whorls at axils (average of 5 leaves).

*Leaf surface*.—Smooth to moderately glossy on upper and lower surface.

*Leaf internode length*.—Average of 3 mm between whorls.

*Leaf size*.—Up to 2 cm in length and 7 mm in width.

*Leaf quantity*.—Average of 40 pair per branch 6 cm in length.

*Leaf color*.—Newly expanded leaves upper surface; 151A and suffused with 33A and margins of 33A, newly expanded leaves lower surface; 151A with very fine margin of 33A, mature leaves upper surface; a blend of 151A and 144B , mature leaves lower surface; a blend of 151A and 138D, fall leaves upper surface; a blend of 34C and 22C, fall leaves lower surface; a blend of 146B, 34C, and 22C.

*Thorns*.—Below each node is a sharp single thorn; average of 6 mm length and 1 mm in width at base, 151D in color and 183A at tip.

*Petiole*.—Rounded in shape, an average of 1 cm in length and 1.5 mm in diameter, 138D in color.

Inflorescence and fruit description:

*Inflorescence type*.—Umbel with an average of 3 flowers per terminal whorl and about 15 clusters per plant.

*Inflorescence size*.—An average of 8 mm cm in depth and 1.4 cm diameter.

*Flower buds*.—Orbicular to globose in shape, color; a blend of 144A and 151A suffused with 187B, petal portion 4D, an average of 3 mm in length and 4 mm in width.

*Flower fragrance*.—None detected.

*Lastingness of inflorescence*.—Inflorescence blooms for about 2 weeks with individual flowers lasting about 5 days, self-cleaning (not persistent).

*Flower quantity*.—An average of 3 flowers per terminal inflorescence.

*Flower size*.—An average of 7 mm in diameter and 5 mm in depth.

*Peduncles*.—An average of 4 mm in length to base of inflorescence and 1 mm in diameter, 144B suffused with 187B in color, glabrous surface, rounded in shape.

*Pedicels*.—An average of 4.5 mm in length and 1 mm in diameter, 144B suffused with 187B in color, glabrous surface.

*Bracts*.—An average of 2, at the base of each flower, held horizontal, ovate in shape, an average of 3 mm in length and 2 mm in width, acute apex, truncate base, color; both surfaces a blend of 144A and 151A suffused with 187C, both surfaces glabrous.

*Calyx*.—Cup shaped, becoming more open with maturity, an average of 7 mm in diameter and 3 mm in depth.

*Sepals*.—6 in two whorls of 3, sepals on outer whorl; orbicular to rotund in shape, entire margin, broadly acute to rounded apex, rounded base, an average of 4 mm in length and 3 mm in width, color; upper and lower surfaces NN155A with center region a blend of 144A and 151A, lower surface is also suffused with 187C, both surfaces glabrous, sepals on inner whorl; petal-like, almost orbicular in shape, entire margin, rounded to erose apex, rounded base, an average of 5 mm in length and 4 mm in width, color; upper and lower surfaces NN155A with center region 1C, apex occasionally suffused with 187C and veins 151A, both surfaces glabrous.

*Petals*.—6 in a single whorl, orbicular in shape, strongly cupped inward, entire margin, rounded to erose apex of each free, cuneate base, an average of 4 mm in length and 3 mm in width, color; upper and lower surface NN155A with center region a blend between 1C and 1D, color not fading, both surfaces glabrous.

Reproductive organs:

*Gynoecium*.—1 pistil, obovoid in shape, about 3 mm in length, style is less than 1 mm in length, and 144B in color, stigma is about 2 mm in diameter and less than 1 mm in length, flattened globose in shape with central depression, and N144A in color, ovary is superior, about 2.5 mm in length and 1 mm in diameter, and 144B in color.

*Androcoecium.*—6 stamens, about 3 mm cm in length, filaments are 4C in color and about 1.5 cm in length, anthers are about 1 mm in length, basifixed, 4B in color, pollen is abundant in quantity and 4C in color.

*Fruit and seed.*—True berry, ovoid in shape, about 5 mm in diameter and 7 mm in length, produced in late summer, 185B in color, seed; 0.5 mm in size and 200A in color.

It is claimed:

1. A new and distinct cultivar of *Berberis* plant named '24kagozam' as herein illustrated and described.

* * * * *